(12) United States Patent
Sanborn et al.

(10) Patent No.: US 9,115,146 B2
(45) Date of Patent: Aug. 25, 2015

(54) PROCESS FOR PRODUCING ISOHEXIDES

(71) Applicant: ARCHER DANIELS MIDLAND COMPANY, Decatur, IL (US)

(72) Inventors: Alexandra Sanborn, Lincoln, IL (US); Brennan Smith, Decatur, IL (US); Joshua Terrian, Lovington, IL (US); Erik Hagberg, Decatur, IL (US); Erin Rockafellow, Decatur, IL (US); Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/596,596

(22) Filed: Jan. 14, 2015

(65) Prior Publication Data

US 2015/0126599 A1    May 7, 2015

Related U.S. Application Data

(63) Continuation of application No. PCT/US2013/063356, filed on Oct. 4, 2013, which is a continuation of application No. PCT/US2013/063347, filed on Oct. 4, 2013, application No. 14/596,596, which is a continuation of application No. PCT/US2013/063351, filed on Oct. 4, 2013.

(60) Provisional application No. 61/720,453, filed on Oct. 31, 2012, provisional application No. 61/720,457, filed on Oct. 31, 2012, provisional application No. 61/720,466, filed on Oct. 31, 2012.

(51) Int. Cl.
   *C07D 493/04*    (2006.01)

(52) U.S. Cl.
   CPC .................................. *C07D 493/04* (2013.01)

(58) Field of Classification Search
   USPC ......................................................... 549/464
   See application file for complete search history.

(56) References Cited

U.S. PATENT DOCUMENTS 7,439,352 B2 * 10/2008 Moore et al. .................. 536/124

* cited by examiner

*Primary Examiner* — Kristin Vajda
(74) *Attorney, Agent, or Firm* — William B. Miller

(57) ABSTRACT

A process is described for producing an isohexide wherein an hexitol or a combination of hexitols is continuously dehydrated in the presence of an acid catalyst under vacuum using a thin film evaporator.

12 Claims, 2 Drawing Sheets

PROCESS FOR PRODUCING ISOHEXIDES

CROSS-REFERENCE TO RELATED APPLICATIONS

This application is a continuing application from, and hereby incorporates by reference, each of copending and commonly-assigned Patent Cooperation Treaty Application Serial No. PCT/US13/63356, filed Oct. 4, 2013 for "Improved Method of Making Internal Dehydration Products of Sugar Alcohols" (hereafter the "WO'356" application", now published as WO 2014/070371), which claims priority of now-abandoned U.S. Ser. No. 61/720,453 filed Oct. 31, 2012; Patent Cooperation Treaty Application Serial No. PCT/US13/63347, filed Oct. 4, 2013 for "Hydrogenation of Isohexide Products for Improved Color" (hereafter the "WO'347" application, now published as WO 2014/070369), which claims priority of now-abandoned U.S. Ser. No. 61/720,457 filed Oct. 31, 2012; and Patent Cooperation Treaty Application Serial No. PCT/US13/63351, filed Oct. 4, 2013 for "Additives for Improved Isohexide Products" (hereafter the "WO'351" application, now published as WO 2014/070370), which claims priority of now-abandoned U.S. Ser. No. 61/720,466 filed Oct. 31, 2012.

TECHNICAL FIELD

The present invention relates generally to the production of isohexides, and more particularly to the production of isosorbide, by the dehydration of a corresponding sugar alcohol or alcohols, respectively. In relation to the production of isosorbide, sorbitol dehydration methods are implicated.

BACKGROUND OF THE INVENTION

Isohexides such as isosorbide, isomannide and isoidide (sometimes referred to as dianhydrohexitols or anhydrosugar alcohols) have been of considerable commercial interest for a number of years. Isosorbide in particular is currently used to a limited extent as a starting material for isosorbide mononitrate and dinitrate, vasodilators used for treating angina pectoris, congestive heart failure and in other similar contexts, but isosorbide and to a lesser extent the other isohexides have long been considered as having the potential for widespread use as biobased monomers, surfactants and other commodity scale, non-pharmaceutical applications. For example, in relation to the large, commodity scale polymer systems in use today, efforts have been made over a number of years to use isosorbide in the manufacture of polyurethanes, polyesters, polycarbonates and polyamides.

Unfortunately, however, it has proven very difficult to make isosorbide in the requisite purity for such polymeric applications (these uniformly require very high purity materials) at any reasonable scale, much less to make isosorbide in the requisite high purity at a reasonable scale and with sustainable economics in relation to the petrochemically-derived materials which have been conventionally used in these applications.

According to Fuertes in U.S. Pat. No. 8,008,477 ("Fuertes"), in fact, for not only polymeric applications but for the majority of the contemplated applications of isosorbide and other internal dehydration products of hydrogenated sugars, in particular, the other isohexides, it is generally required to apply a purification treatment to the compositions resulting directly from the actual dehydration step. This is in particular because any hydrogenated sugar or sugar alcohol subjected to such a step (for example sorbitol) is likely to be converted at least in part to various other coproducts. Fuertes lists these various other coproducts as including, for example: isomers of the said desired product, for example, isomers of isosorbide such as isomannide and isoidide; products which are less dehydrated than the desired product or than its isomers, for example, sorbitans, mannitans or iditans (some of which are terminal products themselves which do not further undergo dehydration); derivatives resulting from the oxidation or more generally from the degradation of the abovementioned products, it being possible for these derivatives to include, for example, when the desired product is isosorbide, coproducts such as deoxymonoanhydrohexitols, monoanhydropentitols, monoanhydrotetritols, anhydrohexoses, hydroxymethylfurfural, or glycerin; derivatives resulting from the polymerization of the abovementioned products; and/or "highly coloured species of a poorly defined nature".

Fuertes observes that, in general, all or some of the various categories of coproducts or impurities mentioned are unavoidably generated to a greater or lesser degree during the actual step of dehydration of the hydrogenated sugar, regardless of the dehydration conditions and of the precautions taken, for example, regardless of the acid catalyst used (whether inorganic acid, organic acid, cationic resin, and the like), the quantity of water or of organic solvent(s) in the initial reaction medium, or of the purity of the hydrogenated sugar, for example sorbitol, composition used as raw material.

Fuertes observes that various technologies had been recommended for obtaining isosorbide of a higher purity given these realities, whether by altering the manner in which the sorbitol dehydration is carried out and/or by applying one or more purification treatments on the crude isosorbide product.

The art discussed by Fuertes includes CA 1178288, which recommends at page 14, lines 3-8 to carry out the dehydration under an inert gaseous atmosphere in order to avoid oxidation reactions, in particular when relatively high temperatures and long reaction times are envisaged.

U.S. Pat. No. 4,861,513 describes a sorbitol dehydration reaction carried out simultaneously in the presence of an inert gas (nitrogen) and a reducing agent (sodium hypophosphite) for the preparation of particular mixtures of polyols, which have a low content (10 to 26%) of isosorbide.

For its part, GB 613,444 describes the production, by sorbitol dehydration in a water/xylene medium, of an isosorbide composition which is then subjected to a treatment of distillation and then of recrystallization from an alcohol/ether mixture.

A purification treatment combining distillation and recrystallization from a lower aliphatic alcohol (ethanol, methanol) was recommended in WO 00/14081. This document moreover indicates that, in the case where distillation is the only purification step contemplated, it is advantageous to carry out the said step in the presence of sodium borohydride.

Fuertes observes in discussing WO 00/14081 that other authors had also recommended that the distillation step be carried out in the presence of a boron-containing compound, in particular of boric acid or of an anionic resin previously charged with borate ions, as described in U.S. Pat. No. 3,160, 641.

U.S. Pat. No. 4,408,061 and EP 323,994 are similar in describing the use of particular dehydration catalysts (gaseous hydrogen halide and liquid hydrogen fluoride, respectively), advantageously combined with carboxylic acids as co-catalysts followed by the distillation of the crude isosorbide or isomannide compositions thus obtained.

U.S. Pat. No. 4,564,692 is described by Fuertes as mentioning, without giving any details, prepurification on "ion exchangers and/or activated charcoal" of isosorbide or isomannide compositions followed, after concentration by evaporation and seeding of crystals of the desired isohexide, by crystallization thereof from water.

EP 380,402 is summarized as describing the dehydration of hydrogenated sugars in the presence of hydrogen under pressure and of particular catalysts based on a combination between copper and a noble metal of Group VIII or gold. These conditions are presented as making it possible to significantly reduce the formation of impurities of a polymeric nature during the actual dehydration step.

EP 915,091 is mentioned as referencing the possibility of further advantageously reducing the genesis of such undesirable polymers, by using acid-stable hydrogenation catalysts during the dehydration step.

U.S. Pat. No. 7,122,661, commonly assigned with U.S. Pat. No. 8,008,477 to Fuertes and naming Fuertes as a co-inventor, describes a process for obtaining isohexide compositions of 99.5% or greater purity and improved storage stability, without necessarily involving a comparatively costly and low yielding post-distillation crystallization step from a solvent medium, through using an ion-exchange step followed by a decolorization treatment step. More particularly, a distilled isohexide composition is described as subjected to treatment with at least one ion-exchange means, which can be a mixed bed of anionic resin(s) and cationic resin(s) or a succession of cationic resin(s) and anionic resin(s), followed by treatment with at least one "decolorizing means". The decolorizing means can be activated charcoal in granular or pulverulent form. In certain embodiments, a second treatment with the decolorizing means is contemplated before the ion-exchange treatment step. Improved stability isosorbide compositions were said to be produced by the process, though the same steps—ion-exchange treatment followed by decolorizing means treatment—were surprisingly said to result in a destabilizing effect when performed in the reverse order.

"Stability" as expressed in the '661 patent referred to the stability of a composition over time in terms of variation of the pH, the conductivity and/or the content of certain impurities, formic acid and ionic species generally being specifically mentioned as possible promoters or indicators of instability not recognized in the listed prior art, col. 5, lines 13-22.

Fuertes concludes his review of the art in U.S. Pat. No. 8,008,477 by observing that even if the prior art methods successfully provided an isosorbide product of the required purity—whether by reducing byproduct formation in the dehydration step and/or by post-dehydration purification measures—nevertheless, the purified compositions thus obtained would degrade over time under conventional conditions of storage temperature, i.e., generally between 0 and 40° C. Specifically, Fuertes reported that the stability of an isohexide composition is "not necessarily correlated" with its purity, and preparation in an inert atmosphere and/or in the presence of sodium borohydride in the dehydration or in the distillation step likewise did not materially improve the stability of these compositions, col. 3, lines 58-67. Rather, "only" the use of specific stabilizing agents in nongaseous form and after the distillation step was helpful for improving the storage stability of isohexide compositions at ambient and moderate temperatures, col. 4, lines 1-14. Suitable "stabilizing agents" are chosen from the group comprising reducing agents, antioxidants, oxygen scavengers, light stabilizers, anti-acid agents, metal-deactivating agents and mixtures of at least any two of such materials, col. 4, lines 48-53. In certain embodiments, an optional further "purification step" was taught following the distillation, an example being the use of both ion exchange and decolorizing means of the type described in the earlier '661 patent.

The '477 patent for its part also defines a "stable composition" more precisely than the earlier, commonly-assigned '661 patent. A "stable composition" in the '477 patent was understood to mean a "composition which, when stored in a noninert atmosphere for a period of at least one month and at a temperature of 40 degrees Celsius, has both a formic acid content of less than 5 ppm and an overall content of monoanhydrohexoses of less than 50 ppm, expressed on a dry weight basis relative to the dry weight of the composition as a whole.

While Fuertes thus aptly describes the challenges faced by those skilled in the art in producing an isosorbide product of the needed purity and further appreciates the additional challenge of the tendency of even high purity isosorbide products to degrade over time under conventional storage conditions, yet as documented in the prior related WO'347, WO'351 and WO'356 applications, nevertheless Fuertes as well fails to fully appreciate the complexity of the dehydration chemistry at work in the process of converting sugar alcohols to their twice-dehydrated products, and how readily undesirable byproducts are formed which will lead to the development of color in a finished, purified isohexide product over time under ordinary storage conditions.

SUMMARY OF THE INVENTION

The present invention in one aspect may be considered a further improvement to the processes described in any or all of the prior WO'347, WO'351 and WO'356 applications, namely wherein sorbitol or another hexitol or a combination of hexitols is continuously dehydrated in the presence of an acid catalyst under vacuum using a thin film evaporator, where "thin film evaporator" as used herein will be understood as comprehensively embracing thin film evaporators, wiped film evaporators, short path evaporators, falling and climbing film evaporators, falling and climbing film plate evaporators and any similar device wherein a fluid moves across or over a heated surface as opposed to being heated in a continuous bulk mass wherein heat is transferred in the main from one portion of the fluid to another. Conducting the dehydration in this manner enables a continuous process to be conducted at comparatively lower temperatures and with a reduced thermal history for the crude dehydration product, leading into the downstream refining steps that must be accomplished to produce a finished isohexide product of the high purity needed for the various contemplated applications for the isohexides. It will be appreciated on consideration of the degradation chemistry and byproducts discussed by Fuertes and others, and documented more fully in the prior WO'347, WO'351 and WO'356 applications, that a lower dehydration reaction temperature and a reduced thermal history will be beneficial in ultimately producing a desired low color and color-stable isohexide product. The crude dehydration product is then processed in this first aspect according to any of the prior WO'347, WO'351 and WO'356 applications.

In one embodiment of the invention, accordingly, prior to the application of any distillation, chromatographic resolution or other known method for working up the crude dehydration product mixture from the thin film evaporator to provide a purified isohexide product, a process as taught in the WO'356 application is employed wherein ionic species in the crude dehydration product mixture are first chromatographically substantially separated from the remainder of the dehydration product mixture, then the remainder undergoes one or more of distillation, chromatography, solvent recrystallization, melt crystallization and solvent washing and filtration to yield a product enriched in at least one isohexide compared to the remainder.

In certain embodiments, the residual material following the substantial separation of ionic species from the dehydration product mixture and following the further processing (to yield the isohexide-enriched product) is recycled to the dehydration step of the manufacturing process.

In another embodiment, a process as taught in the WO'351 application is employed wherein an antioxidant is selected and added to the crude dehydration product mixture prior to the application of any distillation, chromatographic resolution or other known method for working up the crude dehydration product mixture from the thin film evaporator to provide a purified isohexide product. Especially, where distillation is used at least in part to work up the crude dehydration product mixture, an antioxidant additive is chosen that will substantially co-distill with the isohexide and remain therewith in the purified isohexide product.

In yet another embodiment, the substantial separation of ionic species from the crude dehydration product mixture according to the WO'356 application is combined with the addition of the antioxidant according to the WO '351 application prior to any distillation of the crude dehydration product mixture to provide a purified isohexide product.

In another embodiment, a catalytic hydrogenation step is employed as taught in the WO'347 application either before and/or after the further processing of the crude dehydration product mixture from the thin film evaporator to yield an isohexide-enriched product.

In other embodiments, a catalytic hydrogenation step is combined with addition of an antioxidant according to the WO'351 application, with a substantial separation of ionic species from the crude dehydration product mixture according to the WO'356 application or with both of these measures—in the same manner as mentioned in the WO'356 application, for example, without the added feature of conducting the dehydration of sorbitol or another hexitol or a combination of hexitols in a thin film evaporator.

From a more general perspective, understanding that producing a crude dehydration product mixture having a reduced thermal history can be helpful independent of the process improvements offered in the prior WO'347, WO'351 and WO'356 applications, the present invention relates in other embodiments to methods for producing isosorbide (or another isohexide or combination of isohexides) by the dehydration of the corresponding hexitol or hexitols in a thin film evaporator, followed by any conventionally known steps for working up the resultant crude dehydration product mixture to provide a purified product. Thus, for example, a process according to Fuertes (U.S. Pat. No. 8,008,477) or according to the earlier commonly-assigned U.S. Pat. No. 7,122,661 may be employed on the crude dehydration product mixture.

DETAILED DESCRIPTION OF EMBODIMENTS OF THE INVENTION

Figure 1:
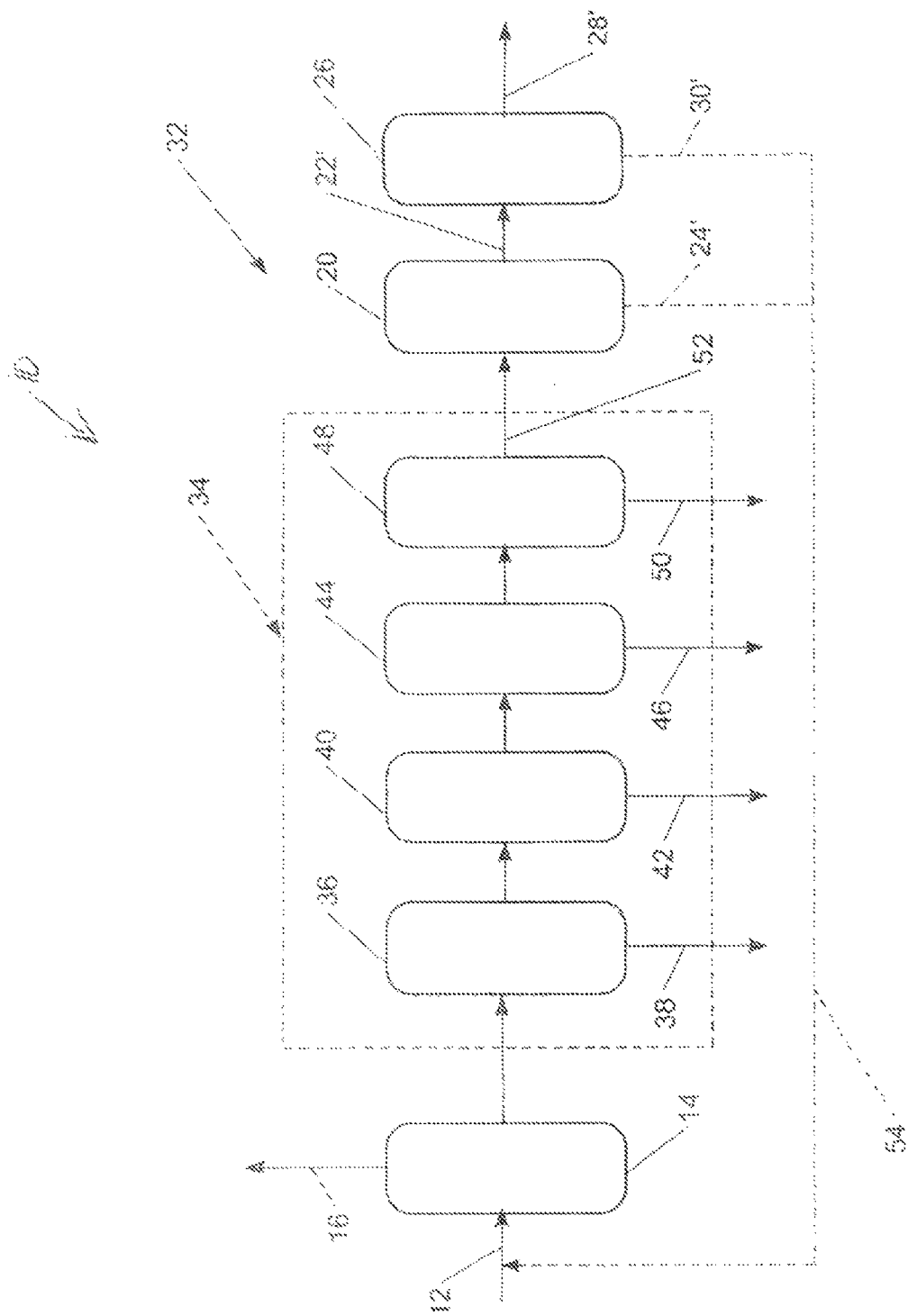
FIG. 1 is a schematic diagram of a process for manufacturing isosorbide from sorbitol in accordance with U.S. Pat. No. 7,439,352, modified in accordance with the WO'356 application to include a chromatographic separation of inorganic salts and other materials from a crude dehydration product mixture and further modified according to the present invention.

Thin film evaporators have been suggested previously for use in processes for producing isohexides by the dehydration of hexitols, though in a different manner.

Briefly, as related very recently in WO 2013/169029 to Kyung et al., published Nov. 14, 2013 for "Method for Preparing High Purity Anhydrosugar Alcohols by Thin Film Distillation", both batch and continuous processes have been known for producing isosorbide from sorbitol (for example).

Batch processes carry out the dehydration in the presence of an acidic dehydration catalyst, commonly under reduced pressure conditions, followed by single-stage or double-stage filtration and "distillation, recrystallization . . . , melt crystallization, activated carbon filtration, ion filtration, etc."

In one referenced continuous process, according to WO 00/14081 to Brinegar et al for "Continuous Process for the Production of Anhydrosugar Alcohols", a process of producing anhydrosugar alcohols involves introducing at least one sugar alcohol or monoanhydrosugar alcohol into a reaction vessel; dehydrating the sugar alcohol or monoanhydrosugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel. The reaction product is described as being separated in one embodiment into water or a lower aliphatic alcohol, with the crude product again being further purified by distillation, recrystallization, melt recrystallization or a combination of these.

A shared difficulty with the batch distillation and simple distillation in either method (according to WO 2013/169029 reference) is that at lower temperatures overly prolonged distillation times are required, while at higher temperatures, shorter distillation times are needed but the risk of thermolysis is correspondingly greater.

The WO 2013/169209 reference in describing this shared difficulty acknowledges the prior teachings of U.S. Pat. No. 7,439,352 to Moore et al. in suggesting an external condenser type thin film evaporator or wiped film evaporator operating under vacuum to facilitate the faster separation of the water from the crude isosorbide product, but suggests an internal condenser type thin film evaporator as an improved alternative.

In any event, in neither reference is there a suggestion whether in relation to an internal or external condenser type thin film evaporator apparatus of using such an apparatus to carry out the initial dehydration under vacuum (and "dehydration" here and elsewhere should be understood as encompassing both the removal of one water from sorbitol to a sorbitan (a monoanhydrosugar alcohol product) or from sorbitan to isosorbide, as well as the removal of two waters from sorbitol to provide the dianhydrosugar alcohol product isosorbide). The use of these devices as an hexitol dehydration reactor rather than merely as a separator affords a number of advantages, particularly but without limitation thereto, in the context of manufacturing isosorbide or isohexides generally on a continuous basis while employing the color improvement and stabilization improvement measures of our prior WO'347, WO'351 and/or WO'356 applications. Especially, conducting the dehydration in this manner desirably enables a continuous process to be conducted at comparatively lower temperatures and a reduced thermal history for the crude dehydration product leading into the downstream refining steps that must be accomplished to produce a finished isohexide product of the high purity needed for the various contemplated applications for the isohexides.

The WO'347, WO'351 and WO'356 applications all proceed from the discovery that whereas the '477 patent indicates that the color stability of an isohexide composition is "not necessarily" related to its purity, there are a number of materials which are or may be present in the crude dehydration product mixture and these impurities do in fact relate to the formation of color in a finished isohexide product, especially on storage as a conventional 100 percent molten product or as a conventional 85 weight percent solution. Further, the formation of these undesirable impurities is exacerbated by extended exposure to elevated temperatures. For the preparation of isosorbide from sorbitol by acid-catalyzed dehydration, these materials can include organic and inorganic salts, acids (for example, formic acid and levulinic acid), acid esters (e.g., sulfate esters from a sulfuric acid catalyzed dehydration step, phosphate esters from phosphoric acid catalyzed dehydration and in general the acid esters from a given oxygen acid catalyzed dehydration step) and their conjugate bases, furanics (e.g., 2-acetylfuran, 5-methylfurfural and various five carbon furanics), oligomeric and polymeric materials from, e.g., acid-catalyzed condensation of various ether functionalized impurities in a crude isosorbide product.

Figure 2:
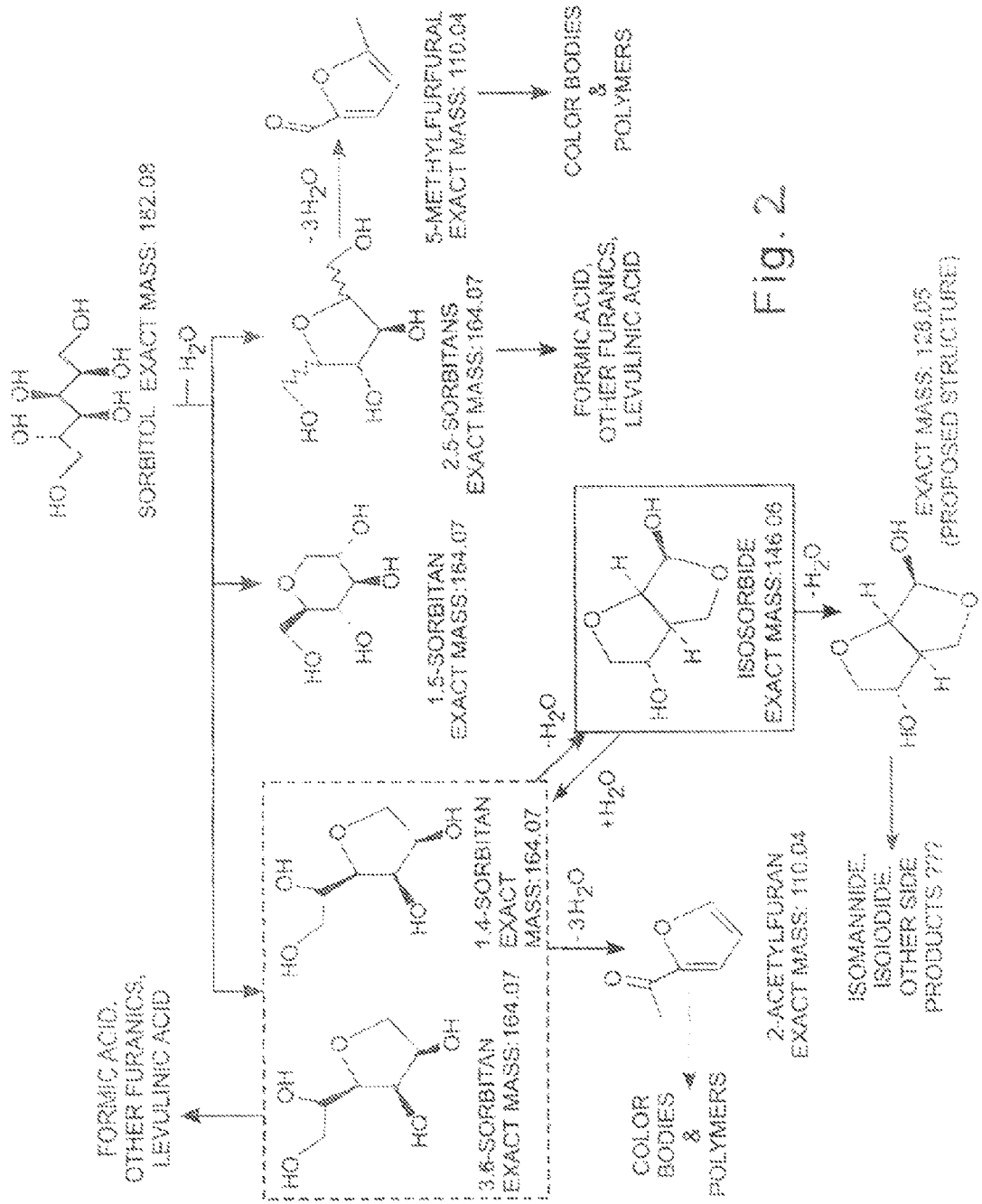
FIG. 2 depicts a proposed dehydration and degradation reaction pathway for a sulfuric acid-catalyzed dehydration of sorbitol, based on information obtained by gas chromatography/mass spectroscopy and by ion chromatography of a crude dehydration product.

More particularly, without being bound and without limiting the present invention in any sense, FIG. 2 depicts a number of materials which have been identified or are believed to be present in the crude dehydration product mixture from a sulfuric acid-catalyzed dehydration of a commercially available sorbitol product and postulates the pathways by which these materials may be formed, based on the confirmed presence of compounds of a given molecular weight as indicated by gas chromatography/mass spectroscopy and, as to the specifically identified sulfate esters, by ion chromatography, as well as based on prior experience with the dehydration of sorbitol.

As will be evident to those skilled in the art on considering the complexity of the illustrated postulated pathways, not all materials present in the crude dehydration product mixture have been identified for FIG. 2 or even attempted to be identified nor quantified, and different (but generally similar) species can be expected in the dehydration of other hexitols by other processes or means than by the use of sulfuric acid.

Nevertheless, whether on an overall basis or on the basis of determining a certain separation of formic acid, which had been identified by Fuertes in U.S. Pat. No. 8,008,477 as indicative of the comparative color instability of an isohexide composition, those skilled in the art will be well able based on the guidance provided herein from the WO'356 application and especially based on the working examples below to carry out a chromatographic separation of those impurities and to optionally undertake additional steps described in greater detail in the WO'347 and WO'351 applications, in order to realize a certain reduction in color and improvement in color stability on storage of a particular finished isohexide product.

In certain preferred embodiments, the residual material following the substantial separation of the impurities and after the further processing to yield the isohexide-enriched product is of a suitable character to be recycled to the dehydration step of the manufacturing process. Recycle of the distillation bottoms from conventional isosorbide manufacturing (to dehydrate or further dehydrate residual sorbitol or monoanhydrohexitols (sorbitans), respectively, in the bottoms) has previously been impractical because of an offsetting negative effect on conversion in the dehydration step, but it was demonstrated in the WO'356 application that the distillation bottoms there was suitable for being recycled. An advantage of the introduction of a thin film evaporator for carrying out the dehydration step that will be appreciated by those skilled in the art, is that the distillation bottoms for recycle in the present inventive process will have a more limited thermal history than the distillation bottoms in the WO'356 application—as will be true also of the products that emerge from the further dehydration step on recycle of the distillation bottoms.

Those skilled in the art will understand that numerous processes have been described for the acid-catalyzed dehydration of sugar alcohols (or monoanhydrosugar alcohols) and the subsequent purification of a crude product, wherein the acid and sugar alcohols (and/or monoahydrosugar alcohols) would be amenable or could be made amenable to the use of a thin film evaporator for carrying out a dehydration step. A detailed treatment of all of these processes consequently need not be undertaken herein.

Turning now to FIG. 1, one illustrative embodiment 10 of an isosorbide manufacturing process is schematically illustrated, as modified to incorporate the improvement of the WO'356 application as well as the further improvement provided by the present invention.

In the first step of the process 10, the sorbitol is melted by standard methods that are known in the art. For example, the sorbitol can be melted by placing it in a 3-neck round bottom flask equipped with an agitator, temperature probe, and vacuum line. Preferably, the sorbitol is heated to at least about 100 degrees Celsius to about 200 degrees Celsius. For sorbitol powder, to provide a specific example, the preferred melting temperature is from about 98 degrees Celsius to about 105 degrees Celsius, while an even more preferred melting temperature is from about 98 degrees Celsius to about 100 degrees Celsius. Alternatively, a sorbitol solution with a high boiling solvent can be contemplated.

A soluble acid catalyst that will facilitate the dehydration of the sorbitol can be added to the molten starting material, as a solution in line at any point prior to a reactor 14 in the form of a thin film evaporator or can be added directly to the reactor/thin film evaporator 14 as an independent feed to be mixed with molten or dissolved sorbitol insitu to provide the sorbitol feed 12 to the reactor/thin film evaporator 14. Sulfuric acid, phosphoric acid, p-toluenesulfonic acid, and p-methanesulfonic acid are examples of soluble strong Bronsted acids that may be used, alone or in combination. As well, as described in U.S. Provisional Patent Application Ser. No. 61/772,642 to Stensrud et al., filed Mar. 5, 2013 for "Process for Acid Dehydration of Sugar Alcohols" (which application is hereby incorporated herein by reference), a water-tolerant Lewis acid could be used, for example, a homogeneous Lewis acid selected from the group consisting of bismuth (III) triflate, gallium (III) triflate, scandium (III) triflate, aluminum triflate, tin (II) triflate and indium (III) triflate.

The amount of catalyst used is indicated as generally being on the order of from about 0.01 equivalents to about 0.15 equivalents by weight. A preferred amount of catalyst is about 0.1 equivalents by weight.

The sorbitol feed 12 is then supplied to the reactor/thin film evaporator 14. As mentioned previously, the reactor/thin film evaporator 14 can be any of a number of known configurations, whether a simple thin film evaporator with an internal condenser (a short path evaporator) or an external condenser, a wiped film evaporator, a rising thin film evaporator, a rising/falling plate evaporator etc., with the objectives of efficient and rapid heat transfer, and a short residence time. The dehydration is carried out under a vacuum to facilitate the rapid removal of water and the use of both lower temperatures and shorter residence times, with the removal of the water product driving the dehydration process forward to completion. The vacuum can range over a pressure of from less than standard atmospheric pressure to less than 0.001 Torr, preferably from about 100 Torr to about 0.01 Torr, with more preferred pressures from about 10 Torr to about 0.1 Torr. As a specific example, a preferred pressure for the dehydration of sorbitol to isosorbide is from about 1 Torr to about 10 Torr. The temperature for the dehydration can be from about 90 deg. C to about 180 deg. C. In certain embodiments, the dehydration temperature can be from 98 deg. C. to about 170 deg. C., especially, from about 120 degrees Celsius to about 150 degrees Celsius. Those skilled in the art will appreciate that the performance of the thin film evaporator 14 may additionally depend to an extent on other attributes, for example, the feed rate of the sorbitol feed 12, condenser temperature, blade speed in a wiped film evaporator and so forth, depending on the type of thin film evaporator used and the particular features of the selected thin film evaporator, but it is considered that the determination of these other attributes will be well within the capabilities of the art.

Pursuant to the teachings of the WO'356 application, one or both of ion exchange and ion exclusion are then employed on the crude dehydration product mixture 18 to remove ionic species before further purification measures are undertaken on the remainder, for example, by the successive distillation steps contemplated according to U.S. Pat. No. 7,439,352 and shown in FIG. 1, as further described below.

In the process 10, more particularly, a crude isosorbide impurity removal system 34 is deployed as taught in the WO'356 application upstream of a first distillation apparatus 20. In the particular embodiment of the system 34 depicted in FIG. 1 and further described hereafter, nanofiltration or ultrafiltration, ion exclusion, ion exchange and carbon or resin bed adsorption work together in combination to remove substantially all of the ionic species from the crude dehydration product mixture 18, as well as removing other species (or the precursors of such species) contributing to the development of color in the finished isohexide product, especially on storage. These various ionic and other species may include, as mentioned previously and as suggested by FIG. 2, such materials as solubilized organic and inorganic salts, formic and levulinic acids, formate and levulinate esters, as well as other acid esters (e.g., sulfate esters from a sulfuric acid catalyzed dehydration step, phosphate esters from phosphoric acid catalyzed dehydration and in general the acid esters from a given oxygen acid catalyzed dehydration step) and their conjugate bases, furanics, oligomeric and polymeric materials and related degradation intermediates or precursors.

In quantitative terms, preferably not more than about 1000 ppm of total ionic species remain in the crude dehydration product mixture entering distillation, on an overall weight basis, after the crude isosorbide impurity removal system 34. More preferably, no more than about 100 ppm remain, and most preferably no more than about 50 ppm remain.

Alternatively, given the numbers of dehydration and degradation products that may be made in the dehydration of sorbitol (as partly demonstrated in FIG. 2), "substantially all" of the color-associated impurities can be considered as having been separated when no more than about 100 ppm remains of formic acid, though more preferably no more than about 10 ppm of formic acid remains after the crude isosorbide impurity removal system 34 and still more preferably no more than about 1 ppm remains.

Returning now to FIG. 1, where both ion exclusion and ion exchange are used, either can be used before the other, with carbon or resin bed adsorption optionally but preferably following in particular to remove nonionic oligomeric and polymeric impurities. Optionally, but also preferably as shown in FIG. 1, nanofiltration or ultrafiltration is used upstream of an ion exclusion step, an ion exchange step or both, primarily to protect the resins from fouling with especially higher molecular weight, oligomeric or polymeric species as may be formed in the crude dehydration product mixture 18, for example, by the proposed reaction pathways shown in FIG. 2.

The particular crude isosorbide impurity removal system 34 illustrated in FIG. 1 includes a first, nanofiltration or ultrafiltration step 36 to remove at least those higher molecular weight, oligomeric or polymeric impurities in the crude dehydration product mixture 18 (as indicated by retentate 38) that have tended in our experiments to precipitate out and foul subsequent ion exchange and/or ion exclusion resins. For the sulfuric acid-catalyzed crude isosorbide product mixtures used below in our examples, we found that membranes having a molecular weight cut-off of about 1,000 to 10,000 were satisfactory, though those skilled in the art will appreciate that for other crude isohexide product mixtures produced by different methods or under different conditions, other nanofiltration or ultrafiltration membranes may be best or may not be economically worthwhile to implement at all. Examples of the membranes we have tried and found useful under our particular conditions include GE Power and Water GE-series, and PW-series polyethersulfone ultrafiltration membranes, Sepro PES5, PES10 polyethersulfone, and PVDF4 polyvinylidine fluoride ultrafiltration membranes.

Where fouling of subsequent ion exchange and/or ion exclusion resins is a concern, other measures may be considered as well as alternatives to the use of nanofiltration or ultrafiltration membranes. For our purposes, the inclusion of a nanofiltration or ultrafiltration step 36 was effective for preventing the fouling, so that we did not undertake to determine whether the fouling was at least in part a function of cooling of the crude dehydration product mixture 18 that reduced the solubility of the higher molecular weight materials in the mixture 18 (which could be addressed by jacketing, insulating, steam tracing and the like) or at least partly related to the pH of the crude dehydration product mixture 18 (which could be addressed by tighter pH control on neutralization).

Following the nanofiltration or ultrafiltration step 36, an ion exclusion step 40 is employed for removing ionic species (42) from the filtered crude dehydration product mixture 18 through simulated moving bed chromatography using at least one strong acid cation exchange resin. Preferred resins are chromatographic grade, gel type resins with a volume median diameter between 290-317 μm, where more than 80% of the particle size range is between 280-343 μm and more than 60% of the particle size range is between 294-392 μm, which are characterized by a crosslink density of less than 12%, more preferably less than 8% and ideally less than 6%, and which are in the cation form corresponding to the highest concentration cation present in the crude dehydration product mixture 18. The ion exclusion step 40 may be conducted in a batchwise, semibatch or continuous manner and may be conducted through a fixed bed arrangement or a continuous simulated moving bed system.

Ion exclusion step 40 is followed by an ion exchange step 44 for removing additional ionic impurities (46), through the use of preferably a fixed bed arrangement including at least one highly crosslinked strong acid cation exchange resin in the hydrogen form and one macroporous, highly crosslinked strong base anion exchange resin in the hydroxide form. As with the materials used for the ion exclusion step 40, while particular examples follow hereafter, various resins of the indicated types are commercially available and known to those skilled in the art, and it will be well within the capabilities of those of ordinary skill in the use of such ion exchange resins to select and use appropriate resins effectively in the ion exchange step 44 to remove additional impurities of the types listed above from the crude dehydration product mixture 18.

A carbon or resin bed adsorption step 48 is then used principally to remove further nonionic oligomeric and polymeric impurities and/or color bodies (50) that may remain. Preferably a fixed bed arrangement with one or more activated carbons is used. Suitable activated carbons include but are not limited to Norit® SA2 steam activated carbon from peat, Calgon CPG®-LF low acid soluble iron content granular activated carbon from coal, Calgon CAL® coal-based granular activated carbon, Nuchar® SN chemically activated, wood-based powdered activated carbon, Norit® RO 0.8 high surface area pelletized activated carbon, Nuchar® WV-B low density, high surface area granular activated carbon, Calgon PCB® activated carbon from coconut shells, Calgon BL® powdered, reagglomerated coal-based activated carbon, Nuchar® RGC high activity, low ash, low soluble iron granular activated carbon, and Nuchar® SA-20 chemically activated, wood-based powdered activated carbon. Suitable adsorptive resins include but are not limited to macroporous styrene-divinylbenzene type resins, for example, Dowex Optipore L493 and Dowex Optipore SD-2 resins.

The remainder 52 of the crude dehydration product mixture 18 following the crude isosorbide impurity removal system 34 is then filtered (not shown) to remove any of the resin(s) and carbon(s) from the system 34 that may be carried over in the remainder 52. The remainder 52 is then further processed to ultimately yield a finished isosorbide product (28' in FIG. 1) which is enriched in the desired isosorbide material compared to the crude dehydration product mixture 18 and which can be used for making additional products or sold. In the particular illustrative embodiment shown schematically in FIG. 1, initially water is removed from the filtered remainder 52 in a dewatering step (not shown) and the remainder 52 is degassed of light gases (not shown). Thereafter enrichment in the isosorbide can be conventionally achieved by known refining methods, for example, through successive distillations in first and second distillation apparatus 20 and 26, respectively, with the first and second distillation apparatus 20 and 26 preferably making use of thin or wiped film evaporation again to minimize further heat history on the desired isosorbide product 28'.

The removal of impurities via system 34 in advance of distilling a crude isosorbide product has been found to provide significantly higher yields (through the prevention of yield losses to, for example, various degradation products formed in the manner suggested by FIG. 2 or otherwise) with lower intrinsic color and improved color stability as compared to where the system 34 is not used, and a crude isosorbide product containing the impurities is distilled. As reported in the WO'356 application, the removal of the impurities also enables a further yield-enhancing refinement, in that isosorbide distillation bottoms (24' and 30' in the illustrative embodiment of FIG. 1 are combined to provide isosorbide distillation bottoms stream or aggregation 54) from the subsequent distillation step can be recycled to the front of the process so that unconverted sorbitol and sorbitan partial dehydration products can be used to make additional isosorbide. Previously, the isosorbide distillation bottoms have not been amenable to being recycled in this manner, as impurities removed by system 34 have tended to adversely affect the dehydration undertaken in the reactor 14.

In one alternative embodiment that may be considered, the isosorbide distillation bottoms containing some sorbitans can be dehydrated separately and not recycled, under conditions optimized for the dehydration of sorbitans rather than sorbitol. In another alternative embodiment, the isosorbide distillation bottoms may have a sufficiently improved color as to be useful directly in certain less demanding isosorbide product end uses and applications. In yet another alternative embodiment that may be considered, sorbitans are themselves useful products for certain applications (e.g., in food products), so that at least some portion of the sorbitans may be removed for these applications from the isosorbide distillation bottoms before recycling the remainder.

In still other embodiments, the substantial separation of ionic species from the crude dehydration product mixture may be combined with the addition of one or more antioxidant additives before the remainder of the crude dehydration product mixture (52 in FIG. 1) is further processed—through one or more of distillation, chromatography, solvent recrystallization, melt crystallization and solvent washing and filtration—to yield an isohexide-enriched product, consistent with the teachings of the WO'351 application. Preferred antioxidants have sufficient volatility to at least partially co-distill with the isohexide, and are highly soluble in the isohexide.

Preferred antioxidants for color-stabilizing isosorbide include di-tert-butyl-4-methoxyphenol (or DTMP, CAS 128-37-0), butylated hydroxyanisole (BHA, mix of 2- and 3-tert-butyl-4-hydroxyanisoles, CAS 25013-16-5), 2,6-dimethoxy-4-methylphenol (DMMP, CAS 6638-05-7) and 2,6-dimethoxy-4-methylphenol (DMMP, CAS 91-10-1). Of these, BHA and DMMP are preferred.

The amount of antioxidant(s) employed can range from as little as 10 parts per million by weight of the remainder. In other embodiments, the amount of antioxidant(s) can be from about 100 parts per million by weight. In still other embodiments, the amount of antioxidant(s) can be from about 300 parts per million by weight of the remainder. Generally the amount added will be just sufficient to provide, in combination with the present invention or with the present invention together with a catalytic hydrogenation procedure to be described hereafter, the improvements in color and in color stability that are needed for a given end use application and for a given isohexide.

In other embodiments, as briefly mentioned above, a process of the present invention—with or without the use of one or more antioxidant additives added subsequent to removing impurities as taught herein but before the remainder of the crude dehydration product mixture is further processed to yield a finished isohexide product—can be combined with a catalytic hydrogenation step conducted before and/or after the further processing to yield an isohexide-enriched product, as further described in greater detail in the WO'347 application.

More particularly, crude dehydration product mixtures and the remainders of crude dehydration product mixtures to which the process of the present invention had been applied may be hydrogenated in the presence of a suitable catalyst, before the crude dehydration product mixture or a remainder of a crude dehydration product mixture is further processed to yield a finished isohexide product for further use or sale. Materials of improved color are produced. Alternatively (or even additionally), an isohexide product following the further processing may be hydrogenated in the presence of a suitable catalyst for improved (reduced) color. Heterogeneous catalysts are preferred, and in combination with the removal of ionic species according to the present invention, hydrogen pressures of less than about 1000 psig and preferably not more than about 600 psig can be effective for providing reduced color products, as further elaborated and demonstrated in the above-referenced, incorporated application.

The color requirements of a given isohexide can vary, of course, from one purchaser to another and from one end use to another. As well, the composition and other attributes (e.g., pH) of the crude dehydration product mixtures themselves can vary according to the methods by which such mixtures have been produced, so that in some instances it may be sufficient to apply a particular solution offered by the present invention or by a commonly-assigned, incorporated reference alone—while in other circumstances it may be necessary to further employ either or both of the measures described in the commonly-assigned, incorporated references. In any event, it is considered that one skilled in the art having the benefit of the present invention and the commonly-assigned, incorporated applications will be well able to determine the technology or combination of technologies needed to accomplish a needed reduction in color and/or improvement in color stability for a given isohexide product and end use.

While particular color requirements may vary as just mentioned, in general, it is expected that finished 100% molten isohexide products made at least in part by means of the present invention will demonstrate an APHA color as determined in accordance with ASTM D1209 of about 100 or less, preferably about 20 or less, more preferably about 15 or less, and especially about 10 or less. In a conventional 85% solution product form, finished isohexide products will preferably demonstrate an APHA color of about 100 or less, preferably about 20 or less, more preferably about 15 or less and especially about 10 or less. Preferably, the color stability of these compositions will be such that, after accelerated aging at 85 degrees Celsius for four weeks in the manner of the examples of the incorporated application related to the antioxidant additives, the APHA color of a 100% molten product will still be less than about 200. Correspondingly, for an 85% solution product, preferably the APHA color will still be less than about 250. Compositions meeting at least the 200 and 250 APHA color criteria for a 100% molten product and an 85% solution product, respectively, will be considered as "color stable" as that term is used herein.

The present invention is further demonstrated by the non-limiting examples that follow:

Examples 1-4

A two inch diameter wiped film molecular (short path) still (Pope Scientific Inc., Saukville, Wis.) was used to dehydrate an aqueous solution of 70 percent sorbitol and 1 percent by weight of concentrated sulfuric acid. This solution was fed through the still with the heated/reaction zone controlled in the range of from 130 degrees Celsius to 140 degrees Celsius. Vacuum was applied to the still and controlled at from 3 to 10 torr. The feed was controlled with an addition valve that had very little control but the approximate feed rate was 0.2 to 1 ml/minute. The blades were spinning at from 160 to 165 rpm. Water from the feed solution and produced by dehydration or sorbitol was collected in a dry ice trap and a crude isosorbide dehydration product was collected from the bottom of the still. Four samples were collected as the dehydration proceeded over the course of about 5 hours, and these were analyzed by high performance liquid chromatography. The results are shown in Table 1 as follows, with all amounts expressed as percentages by weight and the "Total" representing the total weight percentage accounted for by the tabulated materials:

TABLE 1

| Sample | 2,5-sorbitan | 1,4-sorbitan | Isosorbide | Sorbitol | Total |
|---|---|---|---|---|---|
| 1 | 2.487 | 44.412 | 19.53 | 27.067 | 93.496 |
| 2 | 3.558 | 51.802 | 27.24 | 4.514 | 87.114 |
| 3 | 3.791 | 41.615 | 35.572 | 7.284 | 88.262 |
| 4 | 4.817 | 33.209 | 50.733 | 0 | 88.759 |

Example 5

Granular crystalline sorbitol (3660.0 g, 20.091 mol) was weighed into a 5 liter, three neck round bottom flask. The flask, fitted with a thermocouple, mechanical stirrer and condenser, was heated to an internal temperature of 140 degrees Celsius using a temperature controlled heating mantel until the sorbitol was molten. Vacuum to <10 Torr was applied through a 1 liter receiver in a dry ice isopropanol bath. Concentrated sulfuric acid (20.3 g, 0.202 mol) was added through a rubber septum using a glass syringe. The reaction was run with mechanical stirring under vacuum (8.9 Torr) at 139.2 deg C for 100 minutes. The heat was lowered and the temperature reduced to 90.3 deg C. Sodium hydroxide as a 50% solution in water (32.07 g, 0.401 mol) was then added through the septum using a syringe and allowed to stir for at least fifteen minutes. The vacuum was broken and a sample was taken for analysis by GC/FID. Analysis of the resulting crude reaction mixture showed a 99.93% conversion of the sorbitol, a 70.75% mol selectivity to isosorbide and 56.72% weight yield of isosorbide relative to sorbitol. The reaction mixture was then diluted with 1.5 liters of deionized water and filtered through a 0.2 µm filter using a Buchner funnel.

Additional isosorbide was prepared in substantially the same manner in two additional batches, to provide a composited material for the ion exclusion, ion exchange and distillation studies detailed in the following examples. Details of the three batch preparations are found in Table 2 as follows:

TABLE 2

| Rxn Time (min) | Rxn Temp (avg) | Rxn vacuum (avg) | NaOH Added Temp (deg C.) | Acid (wt %) | NaOH/ $H_2SO_4$ (mol) | Rxn water/ sorbitol (mol/mol) | Conversion (%) | Yield (wt %) |
|---|---|---|---|---|---|---|---|---|
| 87 | 139 | 8.4 | 86.7 | 0.53 | 2.02 | 2.81 | 99.9 | 49.8 |
| 90 | 128 | 6.8 | 91.1 | 0.55 | 2.01 | 2.15 | 99.4 | 56.6 |
| 100 | 146 | 8.9 | 90.3 | 0.55 | 1.99 | 2.09 | 99.9 | 56.7 |

Example 6

Separation of Ionic from Non-Ionic Components Using Fixed Bed Ion Exchange Chromatography In a slurry of deionized water, strongly acidic cation exchange resin (DOWEX™ 88 sulfonate functionalized macroporous styrene divinylbenzene strong acid cation exchange resin, The Dow Chemical Company, Midland, Mich.) in the proton form was added to a #25 Ace Glass jacketed chromatography column (25 mm ID×600 mm L) to the 300 cc mark. In a second slurry of deionized water, a strongly basic anion exchange resin (AMBERLITE™ FPA91 CI food grade, macroreticular strong base anion exchange resin, The Dow Chemical Company, Midland, Mich.) in the hydroxide form was added to a #25 Ace glass jacketed chromatography column (25 mm ID×600 mm L) to the 300 cc mark. In a third slurry of deionized water, activated carbon was added to a #25 Ace glass jacketed chromatography column (25 mm ID×600 mm L) to the 300 cc mark. The columns were capped with Teflon adapters and connected in series: 1) cation, 2) anion and 3) carbon, using ⅛" Teflon tubing and Swagelok fittings.

Neutralized isosorbide crude reaction mixture with a composition of approximately 31% by wt isosorbide, 44% by wt sorbitan, 1.7% by wt. sodium sulfate, diluted in deionized water was pumped through the columns using a peristaltic pump at a flow rate of 20 mL/min, at room temperature. The effluent from the columns was dewatered using a rotary evaporator. Analysis by ICP measured 6.2 ppm of residual sodium and 2.4 ppm of residual sulfur (LOD: 0.1 ppm). HPLC/UV analysis of the dewatered ion exchanged crude showed non-detectable carboxylic acids. The final product qualitatively showed significant color reduction, from a dark brown starting material to a very light yellow final material.

Example 7

Separation of Ionic from Non-Ionic Components Using Simulated Moving Bed Ion Exclusion Chromatography In a simulated moving bed chromatography system (SMB) from Calgon Carbon Corp, Pittsburgh, Pa., twelve #11 Ace Glass chromatography columns (11 mm ID×450 mm L) mounted on a PLC controlled carousel were slurry-packed with a strong acid cation exchange resin (DOWEX™ MONOSPHERE™ 99/310 sulfonate functionalized, styrene divinylbenzene strong acid cation exchange resin) in the sodium form. The columns were capped with Teflon fittings and plumbed with 1/16" Teflon tubing into 4 zones. Liquids were distributed through the system using four Eldex positive displacement pumps.

Isosorbide crude reaction mixture neutralized, diluted with deionized water and filtered through a 0.2 μm filter was analyzed by GC/FID and Karl Fischer to have 46.025 wt. pct. of isosorbide, 7.352 wt. pct. of sorbitans, and 34.940 wt. pct. of water. Analysis by IC and ICP of the feed solution showed 1541 ppm formate, 697 ppm sulfate and 1929 ppm sodium.

The isosorbide solution was fed into column six in zone three at a rate of 1.5 mL/min. Deionized water was used as the eluent and fed into column one in zone one at a rate of 3.08 mL/min. Extract composed of 34.81 wt. pct. of isosorbide, 4.513 wt. pct. sorbitan, 179 ppm formate, 122 ppm sulfate, 217 ppm sodium and 54.67 weight percent of water. Water was taken from column two in zone one at a rate of 4.51 mL/min and returned, as enrichment, into column three in zone two at a rate of 1.73 mL/min resulting in a net product flow rate of 2.78 mL/min. Raffinate composed of 1.748 wt. pct. of isosorbide, 1.659 wt. pct. of sorbitan, 1152 ppm formate, 480 ppm sulfate, 1812 ppm sodium and 86.45 wt pct. of water, was removed from column ten in zone three at a rate of 3.23 mL/min and returned into column eleven in zone four at a rate of 1.43 mL/min resulting in a net raffinate flow rate of 1.8 mL/min.

Countercurrent rotation of the SMB column carousel occurred stepwise at 10.75 minute intervals. The entire system revolved 7.3 times during the course of the 15.6 hr experiment. Based on GC/FID analysis of the samples taken from the extract and raffinate streams, the yield of isosorbide from the separation was 96.9 wt. pct. with a normalized purity increase from 86 percent to 88 percent due to loss of sorbitans into the raffinate. Total ion exclusion of the formate, sulfate and sodium was 80.6 percent by weight, 71.7 percent by weight and 84.4 percent by weight, respectively. Surprisingly, it was observed that the bulk of the color bodies from the feed eluted in the raffinate, resulting in a significantly improved color of the isosorbide solution from dark black, non-transparent feed to a light yellow, completely transparent extract.

Example 8

Separation of Ionic from Non-Ionic Components Using Combined Simulated Moving Bed Ion Exclusion and Ion Exchange Chromatography Extracts from a series of simulated moving bed ion exclusion runs conducted substantially as described in Example 7 were combined, yielding about 5 gallons of light yellow isosorbide solution in water having a composition of 29.45 percent by weight of isosorbide, 3.31 weight percent of sorbitans, 133 ppm of formate, 270 ppm of sulfate, 193 ppm of sodium, and 67.14 percent by weight of water. DOWEX™ 88 sulfonate functionalized macroporous styrene divinylbenzene strong acid cation exchange resin in the proton form was slurried with deionized water and added to a 5 liter fixed-bed ion exchange column to the 4 liter mark. DOWEX™ 22 strong base anion exchange resin in the hydroxide form was slurried with deionized water and added to a 5 liter fixed-bed ion exchange column to the 4 liter mark. The ion-excluded isosorbide solution was pumped through the fixed-bed cation and anion exchange columns in series using a peristaltic pump at a flow rate of approximately 40 mL/min. The effluent from the columns was collected, dewatered using a rotovap, and analyzed. The composition of the combined ion-excluded, ion-exchanged isosorbide mixture was 72.20 wt percent isosorbide, 8.12 wt percent sorbitans, 0.8 ppm formate, non-detectable ppm of sulfate, 38 ppm of sodium, 5.63 wt percent of water.

Example 9

Distillation of the Ion Excluded, Ion Exchanged Crude Isosorbide Reaction Mixture by Thin Film Evaporator (TFE), with Antioxidant Addition Approximately 3078.86 g of the ion-excluded, ion-exchanged, rotovapped isosorbide solution from Example 8 was added to a five liter, three neck round bottom flask fitted with a thermocouple, magnetic stir bar and condenser. The solution was heated to 110 deg C using a temperature controlled heating mantel and vacuum was applied through the condenser to 5 Torr. The residual 5.63 wt pct. of water was evaporated from the solution and the vacuum was broken.

2,6-Di-tert-butyl-4-methoxyphenol (1.9415 g, Sigma Aldrich 97%) was added to the hot stirring isosorbide solution under nitrogen and allowed to dissolve. The reaction mixture was cooled to room temperature, bottled and shipped to Pope Scientific, Inc. in Saukville, Wis. for distillation.

The ion-excluded, ion-exchanged and antioxidant-treated crude isosorbide reaction mixture was initially passed through a degasser, configured with an external condenser, to remove residual water, low-boiling compounds, and dissolved gases prior to distillation on the thin film evaporator. The temperature for the degassing was held at 120 degrees Celsius, the condenser temperature was maintained at 35 deg C and vacuum was set at 15 mm Hg. The isosorbide was fed at 1021 grams/hr, resulting in 1.5 grams of distillate and 1105.0 grams of residue collected.

Degassed isosorbide residue having a composition of 83.81 percent by weight of isosorbide, 0.19 percent by weight of isomannide, 0.07 percent by weight of isoidide, 12.22 percent by weight of sorbitans, and 600 ppm DTMP was then fed into a 2" thin film evaporator (TFE) configured with an internal condenser, at a flow rate of 711 grams/hr. The skin temperature of the main TFE housing was kept at 170 degrees Celsius. Vacuum was held at approximately 1.2 mm Hg. The internal condenser was kept at 75 degrees Celsius. Distillate (135 grams) and residue (31.0 grams) from the TFE were collected and analyzed by GC/FID and by LC/UV/RID. The composition of the isosorbide distillate was 99.53 percent by weight of isosorbide, 0.17 percent by weight of isomannide, 0.08 percent by weight of isoidide, 0.20 percent by weight of sorbitans, and 197 ppm of DTMP. The neat isosorbide distillate color measured 6 on an APHA color scale. The composition of the isosorbide residue was 13.09 percent by weight of isosorbide, 0.00 percent by weight of isomannide, 0.10 percent by weight of isoidide, and 64.51 percent by weight of sorbitans. The mass yield of the distillation based on analysis of distillate and residue samples was 97.1 percent.

A series of additional 2" TFE (thin film evaporator) distillations of the same isosorbide degassed feed described above were completed in which all conditions were held nearly constant and evaporator temperature was increased incrementally. Results of the distillation experiments can be seen in Table 3. Yields of the TFE distillates from reaction mixtures having the ionic content reduced to nondetectable or near non-detectable levels prior to distillation were significantly higher, and color was significantly lower than historical values in which the ionic species were not first removed.

TABLE 3

|  | Sample #1 | Sample #2 | Sample #3 | Sample #4 | Sample #5 | Sample #6 |
|---|---|---|---|---|---|---|
| Pass 2 (Product Distillation) | | | | | | |
| Evaporator Temperature, ° C. | 150.0 | 155.0 | 160.0 | 165.0 | 170.0 | 175.0 |
| Condenser Temperature, ° C. | 75.0 | 75.0 | 75.0 | 75.0 | 75.0 | 75.0 |
| Vacuum, mm Hg | 1.250 | 1.250 | 1.250 | 1.200 | 1.200 | 1.200 |
| Feed Rate, g/hr | 714 | 788 | 739 | 762 | 711 | 665 |
| Sampling Time, Minutes | 19 | 16 | 19 | 10 | 14 | 12 |
| Total, g | 226.0 | 210.0 | 234.0 | 127.0 | 166.0 | 133.0 |
| Distillate, g | 138.0 | 127.0 | 138.0 | 98.0 | 135.0 | 113.0 |
| Residue, g | 88.0 | 83.0 | 96.0 | 29.0 | 31.0 | 20.0 |
| Distillate Analysis | | | | | | |
| Color (APHA) | 5 | 5 | 6 | 6 | 6 | 6 |
| DTMP (ppm) | 375 | 278 | 240 | 222 | 197 | 159 |
| isosorbide | 99.64% | 99.70% | 99.72% | 99.62% | 99.53% | 99.28% |
| isomannide | 0.23% | 0.20% | 0.19% | 0.17% | 0.17% | 0.15% |
| isoidide | 0.00% | 0.00% | 0.00% | 0.06% | 0.08% | 0.08% |
| total sorbitans | 0.10% | 0.08% | 0.06% | 0.12% | 0.20% | 0.47% |
| Residue Analysis | | | | | | |
| isosorbide | 61.34% | 59.87% | 60.23% | 28.27% | 13.09% | 9.60% |
| isomannide | 0.00% | 0.00% | 0.00% | 0.00% | 0.00% | 0.00% |
| isoidide | 0.11% | 0.11% | 0.12% | 0.12% | 0.10% | 0.08% |
| total sorbitans | 27.86% | 29.55% | 30.67% | 56.69% | 64.51% | 67.05% |
| isosorbide mass yield (%) | 71.8% | 71.8% | 70.4% | 92.3% | 97.1% | 98.3% |

Example 10

Distillation of the Ion Exchanged Isosorbide Crude Reaction Mixture by Thin Film Evaporator (TFE) with Recycle of TFE Bottoms Containing No Salts A crude isosorbide product mixture which had been neutralized, diluted, filtered and treated with a series of fixed bed ion exchange resins to remove ionic compounds to non-detectable levels, was then dewatered using a rotary evaporator. The dewatered feed, containing approximately 31.9 percent by weight of isosorbide and 51.9 percent by weight of sorbitans, was then distilled using a 2" POPE thin film evaporator (TFE) having an internal condenser. The feed was added drop-wise at approximately 0.61 grams/min using a glass, pressure equalized addition funnel equipped with a needle valve. The feed was kept at approximately 70 degrees Celsius using heat tape and insulation. The skin temperature of the main TFE housing was kept at 160 degrees Celsius. Vacuum was held at approximately 4.5 Torr using a vacuum controller applied through an external cold trap filled with dry ice and isopropanol to collect volatiles (e.g. residual water). The internal condenser was kept at 82 deg C using a recirculating bath filled with propylene glycol/water. Spring-loaded Teflon blades rotating at 504 RPM produced a thin film on the inner wall.

Distillate (40.9 g) and residue (84.76 g) from the TFE were collected and analyzed by GC/FID at 89.4 percent and 0.88 percent by weight of isosorbide, respectively, putting the mass yield of isosorbide for this distillation at 98.0 percent by weight.

The still bottoms (84.76 g) were collected and analyzed using GC/FID at 81.1 percent by weight of sorbitans and 0.18 percent by weight of sorbitol. A fraction of the still bottoms (22.9 g) enriched in 1,4-sorbitan was combined with granular crystalline sorbitol (20.0 g, 0.110 mol) in a 2 neck, 100 mL round bottom flask which had been fitted with a rubber septum, short path condenser and magnetic stirring. The mixture was stirred and heated under vacuum until homogeneous, then dehydrated with concentrated sulfuric acid (0.223 g, 0.002 mol) at 140 degrees Celsius and 1 Torr over a period of approximately 180 minutes. The result was a 99.9 percent conversion of the sorbitol, an 89.3 percent conversion of the 1,4-sorbitan, and a 75.1 percent mol selectivity to isosorbide. Historically, distillate bottoms from crude reaction feeds containing ionic species recycled into fresh isosorbide reactions have failed to achieve total conversions above 50%.

What is claimed is:

1. A process for producing an isohexide, wherein a hexitol is continuously dehydrated in the presence of an acid catalyst under vacuum using a thin film evaporator to produce a crude dehydration product mixture including the isohexide dehydration product from the hexitol.

2. A process according to claim 1, further comprising chromatographically substantially separating ionic species from the crude dehydration product mixture, then subjecting the remainder to further processing to yield a product enriched in one or more isohexides compared to the remainder.

3. A process according to claim 2, wherein a residual material following the dehydration, chromatographic separation and further processing steps, containing one or more unconverted hexitols, one or more monodehydrated materials from the one or more hexitols or both unconverted and monodehydrated materials is recycled to the dehydrating step.

4. A process according to claim 2, wherein the further processing includes one or more of distillation, chromatography, solvent recrystallization, melt crystallization, and solvent washing and filtration.

5. A process according to claim 2, further comprising adding at least one antioxidant to the remainder before the further processing.

6. A process according to claim 5, further comprising hydrogenating one or both of the remainder of the crude dehydration product mixture and the product enriched in one or more isohexides with a source of hydrogen in the presence of a catalyst.

7. A process according to claim 2, further comprising hydrogenating one or both of the remainder of the crude dehydration product mixture and the product enriched in one or more isohexides with a source of hydrogen in the presence of a catalyst.

8. A process according to claim 6, further comprising contacting the remainder with at least one adsorbent.

9. A process according to claim 8, further comprising passing the crude dehydration product mixture passes through at least one nanofiltration or ultrafiltration membrane before it is chromatographically processed.

10. A process according to claim 7, further comprising contacting the remainder with at least one adsorbent.

11. A process according to claim 10, further comprising passing the crude dehydration product mixture passes through at least one nanofiltration or ultrafiltration membrane before it is chromatographically processed.

12. A process according to claim 2, wherein chromatographically substantially separating ionic species from the remainder of the crude dehydration product mixture comprises ion exclusion chromatography, ion exchange chromatography or both ion exclusion and ion exchange chromatographic methods.

* * * * *